United States Patent [19]
Carden

[11] 3,973,564
[45] Aug. 10, 1976

[54] ANAESTHETIST'S RESPIRATION APPARATUS

[75] Inventor: Edward Carden, Stockport, England

[73] Assignee: Dupaco Incorporated, San Marcos, Calif.

[22] Filed: Aug. 8, 1974

[21] Appl. No.: 495,658

[52] U.S. Cl............................ 128/202; 128/145.6; 128/145.8; 128/188
[51] Int. Cl.² ...................................... A61M 16/00
[58] Field of Search............. 128/202, 145.5–145.8, 128/188

[56] References Cited
UNITED STATES PATENTS

| | | | |
|---|---|---|---|
| 3,046,979 | 7/1962 | Andreasen........................... | 128/202 |
| 3,256,876 | 6/1966 | Elam.................................... | 128/188 |
| 3,537,450 | 11/1970 | Fox....................................... | 128/145.6 |
| 3,556,097 | 1/1971 | Wallace............................... | 128/188 |
| 3,814,091 | 6/1974 | Henkin................................ | 128/188 |
| 3,901,230 | 8/1975 | Henkin................................ | 128/188 |

FOREIGN PATENTS OR APPLICATIONS
1,193,522   6/1970   United Kingdom.................. 128/188

*Primary Examiner*—Robert W. Michell
*Assistant Examiner*—Henry J. Recla
*Attorney, Agent, or Firm*—Christie, Parker & Hale

[57] ABSTRACT

Respiration apparatus, for anaesthetist's use, to minimize gas consumption by providing for a patient to rebreath deadspace gas (i.e. the gas previously present in the trachea, mouth and bronchial tree and which has not previously undergone change) comprises a housing enclosing an expansible container to which fresh gas is supplied by a fresh gas supply duct and also to the housing outside the container by way of a non-return valve which permits flow only from the respiration tube into the housing, adjustment means being provided to permit adjustment of the extent by which the container may expand.

7 Claims, 10 Drawing Figures

ANAESTHETIST'S RESPIRATION APPARATUS

This invention concerns anaesthetist's respiration apparatus and has for its object to provide a form of such apparatus constructed so that (a) a patient, treated by use of the apparatus, will rebreathe his deadspace gas (i.e. the gas which has not undergone change and normally occupies the trachea, mouth and bronchial tree); (b) it is unnecessary for soda lime to be incorporated therein for absorbing carbon dioxide; (c) the fresh gas needed to be supplied to the apparatus can be as low as seventy-five per cent of the predicted minute volume without build-up of carbon dioxide in the patient; (d) in which the tidal volume as supplied to the patient can readily be adjusted in a particularly simple manner; (e) by use of which a patient may breathe spontaneously, be assisted, or have his respiration fully controlled; and (f) in which all his excess and spent gas from the apparatus can be extracted so as not to contaminate the operating room in which the apparatus is being used or personnel in such room.

Briefly summarized in terms of its structural aspects, the present invention provides an anaesthetist's respiration apparatus which comprises a housing which in turn encloses an expansible and contractible container. The housing defines a continuously open and unvalved fresh gas supply passageway to the interior of the container. A respiration tube, adapted for providing a respiration gas supply to a patient, has a continuously open connection to the interior of the container. The respiration tube is also connected by a branch connection therefrom to the housing outside of the container by way of a non-return valve which permits gas flow only in the direction from the respiration tube into the housing. The volume within the housing, and within the respiration tube between the branch connection and the container, comprises a reservoir for an initial volume of gas exhaled by a patient. Means are provided for adjusting the extent by which the container may expand. An unvalved outlet opening is provided from the housing outside of the container for flow from the housing of gas exhaled by a patient in an amount in excess of said initial volume, which excess gas is communicated to the housing externally of the container via the branch connection and the non-return valve.

The expansible and contractible container is conveniently in the form of a bellows; the adjustment means may then comprise a stop provided, for example, on the inner end of an adjustable rod extending through the wall of the housing.

The respiration tube may, if desired, be connected to the gas supply tube by way of a filter.

In a preferred embodiment of the apparatus of the invention, an outlet of the housing is provided with a valve arrangement having a connecting passageway which is connected to the outlet, a vacuum passageway adapted to be connected to suction means, a ventilator passageway for connection to an automatic ventilator, a bag passageway for connecting to a self-inflating bag, and a vent passageway which opens to atmosphere, the valve arrangement providing for:

a. increase in pressure in the bag passageway causing such passageway to connect with the connecting passageway;

b. decrease in pressure in the bag passageway causing such passageway to connect with the vent passageway;

c. increase in pressure in the connecting passageway causing such passageway to connect with the vacuum passageway;

d. increase in pressure in the ventilator passageway causing such passageway to connect with the connecting passageway; and e. decrease in pressure in the connecting passageway causing such passageway to be opened to the vent passageway.

The invention will be described further, by way of example, with reference to the accompanying drawings, in which.

Figure 1:
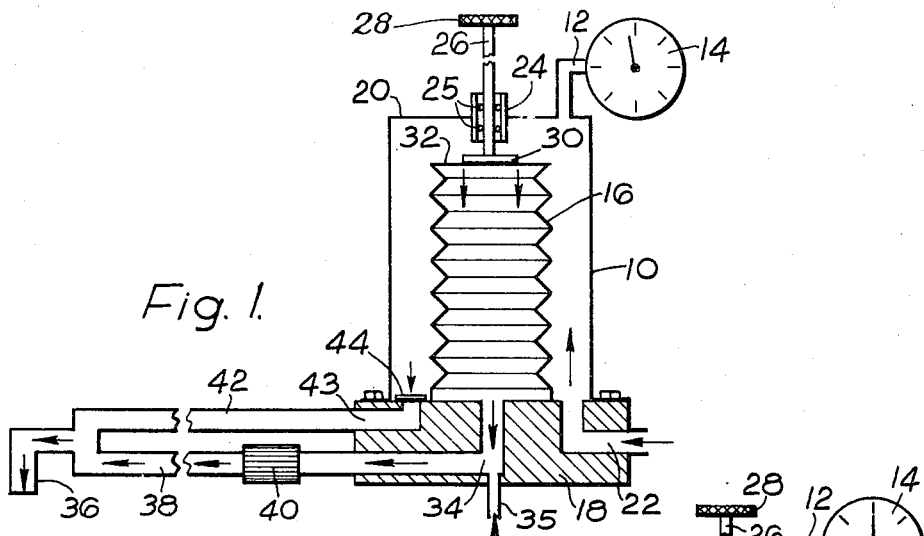
FIG. 1 is a diagrammatic cross-sectional view illustrating a first embodiment of the respiration apparatus of the invention in its condition corresponding to inspiration by a patient.

Referring firstly to FIGS. 1 to 4 of the drawings, the preferred embodiment of the anaesthetist's respiration apparatus conforming to the invention illustrated therein comprises an exterior generally-cylindrical housing 10 connected by a gauge line 12 to a pressure gauge 14. The housing 10 encloses an expansible and contractible container in the form of a bellows 16 which is arranged substantially axially of the housing 10 and is fixedly connected to one end wall provided by a detachable bottom closure plate 18 of such housing 10.

Provided in the bottom closure plate 18 of the housing 10 is an outlet duct 22 which simply opens the interior of the housing 10 to atmosphere.

Set centrally in the other end wall 20 of the housing, which end wall 20 may be integrally formed, is a gland 24 through which extends adjustment means in the form of a rod 26 provided on its outer end with a knurled knob 28. At its inner end, the rod 26 carries a stop in the form of a disc 30 which confronts adjacent free end 32 of the bellows 16. As shown, the rod 26 is externally smooth and is sealed relative to the gland 24 by sealing rings 25 which so frictionally engage the rod 26 as to ensure that it remains in any axially-adjusted position into which it may be shifted. The rod 26 could, alternatively, be externally threaded to engage with corresponding threads in the gland 24 in which case axial adjustment of the rod 26 can be achieved by rotation thereof.

A gas supply duct 34, in the bottom plate 18, connects with the interior of the bellows 16, and is connected to an appropriate fresh gas supply machine (not shown), by way of an inlet 35.

A respiration tube 36 adapted for providing a respiration gas supply to a patient (e.g. by being connected to an endotracheal tube or a mask, neither of which are shown in the drawings) is connected by way of a fresh gas tube 38 with the gas supply duct 34. The fresh gas tube 38 may optionally incorporate a filter 40.

The respiration tube 36 is also connected with the interior of the housing 10, outside the bellows 16, by way of an expiration tube 42 and an expiration duct 43 in the bottom plate 18. The expiration duct 43 is fitted with a dead-weighted non-return valve 44 which permits gas flow only in the direction from the respiration tube 36 into the interior of the housing 10 outside the bellows 16 only upon a predetermined pressure being exceeded in the expiration duct 43.

Figure 2:
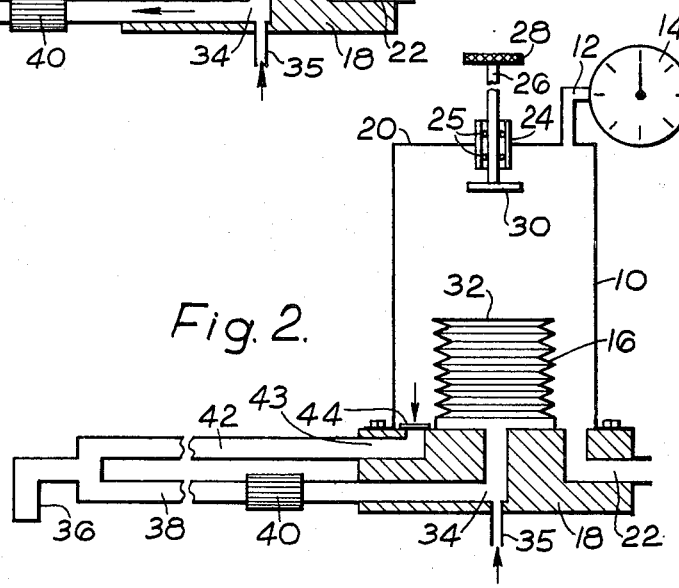
FIG. 2 is a view similar to FIG. 1 but showing the condition of the apparatus at the end of inspiration.
Figure 3:
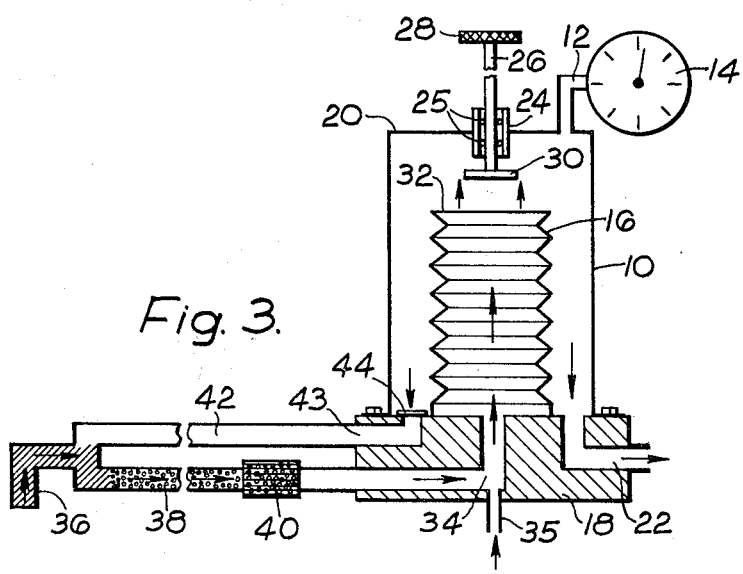
FIG. 3 is a view similar to FIGS. 1 and 2 but showing the condition of the apparatus during exhalation by the patient.

Assuming the apparatus to be connected to a patient, not shown, by way of the respiration tube 36 and fresh gas to be supplied to the gas supply duct 34 by way of the inlet 35, the operation of the apparatus is as follows. Referring firstly to FIG. 1, upon the patient breathing in, at least some fresh gas is inhaled by way of the fresh gas tube 38 and the filter 40, and the resultant reduction in pressure in the fresh gas tube 38 and the bellows 16 causes at least partial collapse of such bellows 16. FIG. 2 shows the apparatus at the end of inspiration by the patient, the bellows 16 being shown collapsed partially.

Upon the patient now exhaling, the exhaled gas preferentially feeds back by way of the fresh gas tube 38 and the gas supply duct 34 to the bellows 16, because of the presence of the dead-weighted non-return valve 44 in the expiration duct 43. Initially, therefore, the bellows 16 expands again as has been indicated in FIG. 3 until such time as the free end 32 of the bellows 16 encounters and is arrested by the stop disc 30.

Figure 4:
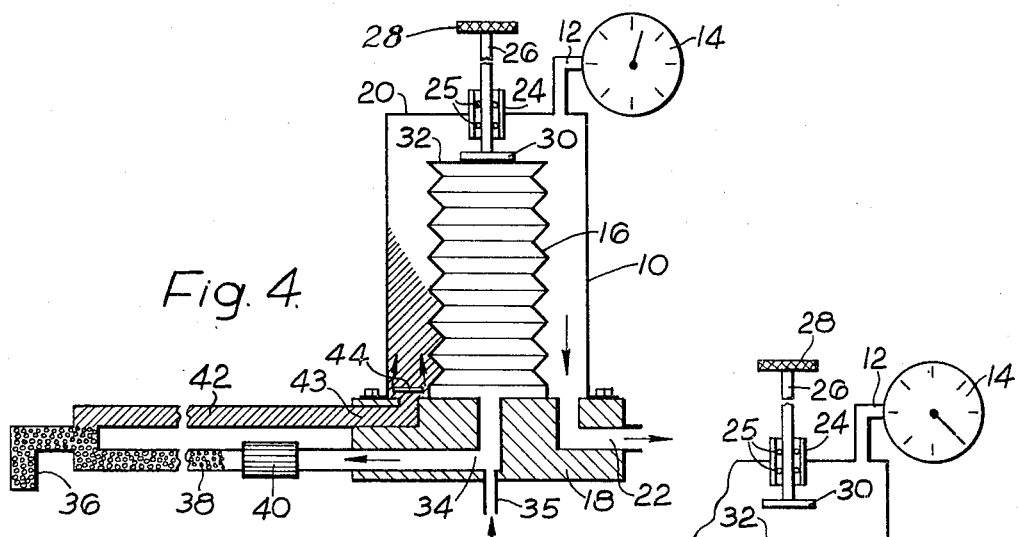
FIG. 4 is a view similar to FIGS. 1, 2 and 3 but showing the apparatus at the end of exhalation.

So soon as the free end 32 of the bellows 16 meets the stop disc 30, further expansion of the bellows 16 is prevented. As a result the pressure then rises in the fresh gass tube 38, gas supply duct 34, bellows 16, expiration tube 42 and expiration duct 43 sufficiently to open the valve 44 which then permits exhaled gases to enter the housing 10 outside the bellows 16 and thence to escape to atmosphere by way of the outlet 22, as shown in FIG. 4.

If the rate of the fresh gas flow is appropriately adjusted, it can be achieved that only the gas from the patient's alveoli will be vented to atmosphere by way of the housing 10 and the outlet 22, and dead-space gas from the patient's trachea, mouth and bronchial tree, which has not undergone any change in each breathing cycle, is retained within the apparatus ready to be inhaled by the patient upon his next inspiration. This dead-space gas is, of course, equally as good as fresh gas being fed to the apparatus. Accordingly, with the apparatus as described, the actual rate at which fresh gas needs to be supplied to the apparatus will always be less than (usually about 70% of) the theoretical or preducted minute volume of the patient, yet the patient does not rebreathe alveolar gas.

Referring now to FIGS. 5 to 10 of the drawings, these figures illustrate a second embodiment of the apparatus of the invention, which is obtained by modification of the apparatus of FIGS. 1 to 4. Accordingly, similar reference numerals have been allocated to those parts of this embodiment which are substantially identical with those already described.

Figure 5:
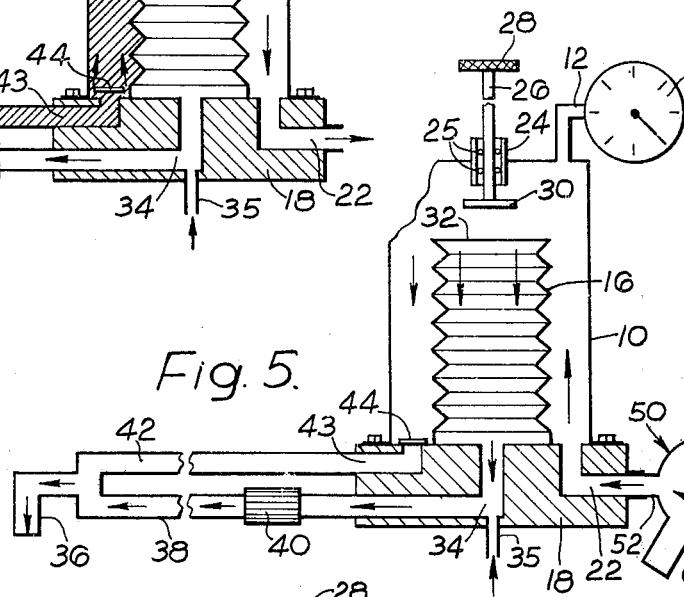
FIG. 5 is a diagrammatic cross-sectional view illustrating a second embodiment (which can be obtained by modification of the embodiment of FIGS. 1 to 4) of the respiration apparatus of the invention in its condition corresponding to inflation of the patient's lungs in using the apparatus for manual ventilation of the patient.
Figure 6:
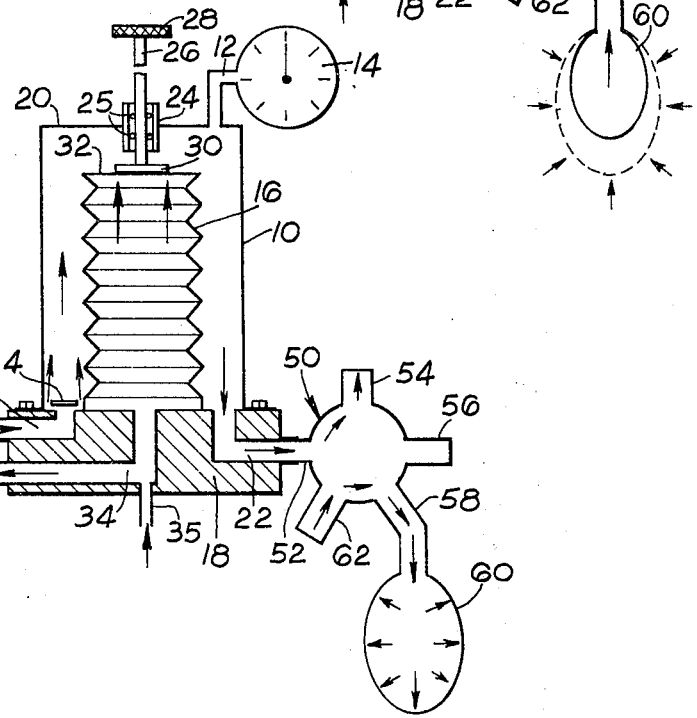
FIG. 6 is a view similar to FIG. 5 but showing the condition of the apparatus corresponding to exhalation in using the apparatus for manual ventilation of the patient.
Figure 7:
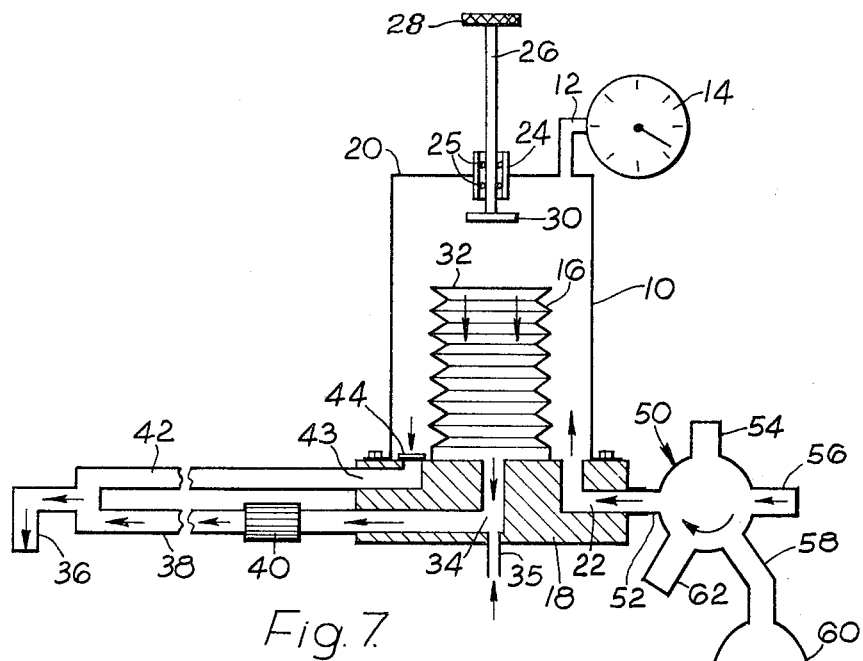
FIG. 7 is a view similar to FIGS. 5 and 6 but showing the apparatus in its condition corresponding to inflation of the patient's lungs in using the apparatus for automatic ventilation of the patient.
Figure 8:
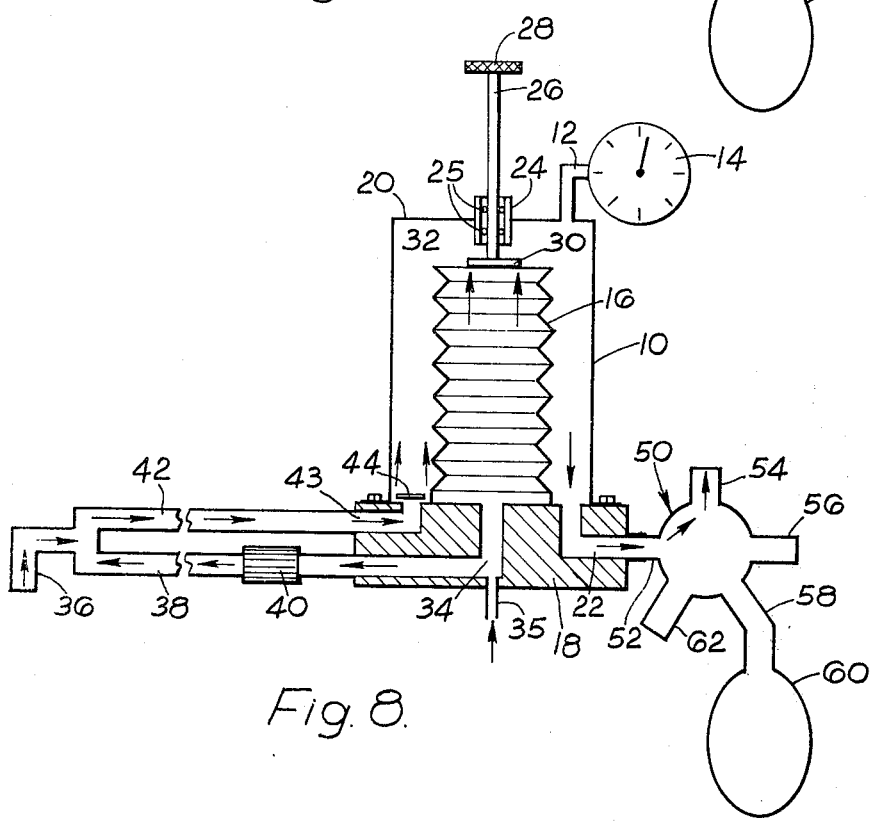
FIG. 8 is a view similar to FIG. 7 but showing the condition of the aparatus corresponding to exhalation in using the apparatus for automatic ventilation of the patient.
Figure 9:
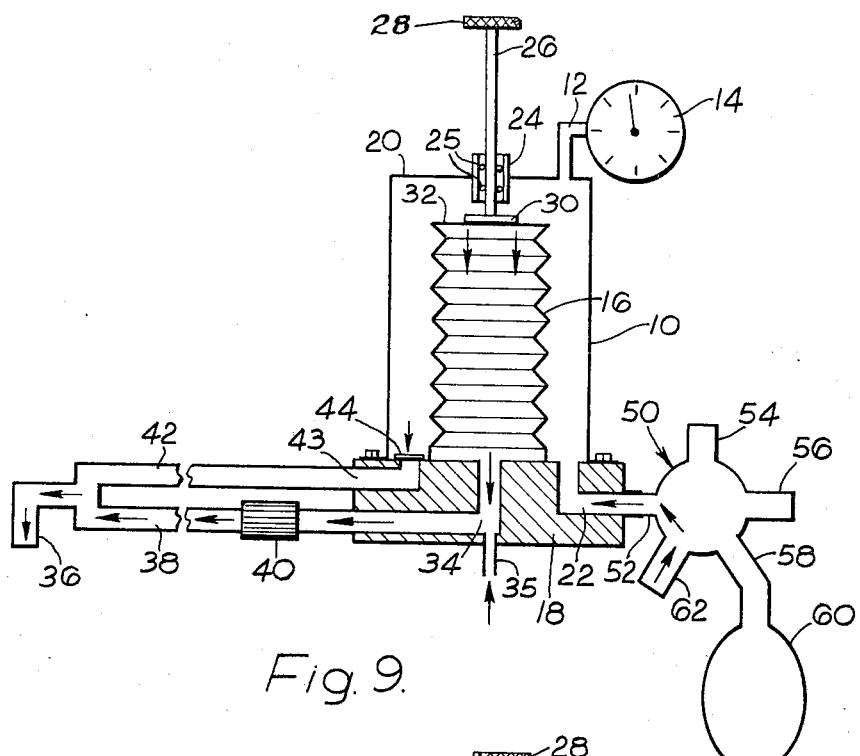
FIG. 9 is a view similar to FIGS. 5 to 8 but showing the apparatus in operation with spontaneous breathing of the patient, during inhalation by the patient.
Figure 10:
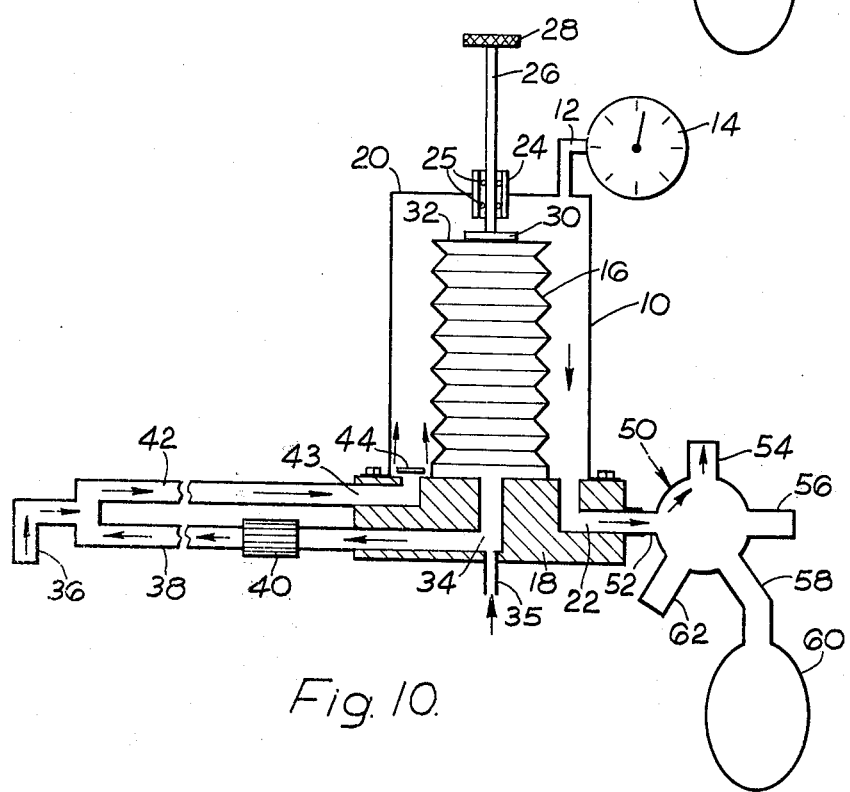
FIG. 10 is a view similar to FIG. 9 but showing the apparatus during exhalation.

As shown, in this embodiment, a valve assembly which is illustrated schematically and indicated generally by the reference numeral 50 is connected to the outlet 22. This valve has five passageways, namely connecting passageway 52 which is connected to the outlet 22; vacuum passageway 54 which is connected to a vacuum line (not shown); ventilator passageway 56 which is connected to an anaesthetist's automatic ventilator (not shown) such as that described in the specification of my prior United Kingdom Pat. No. 1207661; a bag passageway 58 connected to a self-inflating bag which is illustrated diagrammatically at 60; and a vent passageway 62 which opens to atmospheric air. The vent passageway 62 may alternatively be located in the bottom of the self-inflating bag 60 in which case it will be provided with its own automatically-operating non-return valve member. This valve assembly is set up to operate automatically to provide for the following circumstances:

a. Upon increase in pressure in the self-inflating bag 60 and the bag passageway 58, the latter is connected to the connecting passageway 52, as shown in FIG. 5;

b. Upon decrease in pressure in the self-inflating bag 60 and the bag passageway 58, the latter is opened to the vent passageway 62, as shown in FIG. 6;

c. Upon increase in pressure in the connecting passageway 52, the latter is connected to the vacuum passageway 54, as shown in FIGS. 6, 8 and 10;

d. Upon increase in pressure in the ventilator passageway 56, the latter is connected to the connecting passageway 52, as shown in FIG. 7; and e. Upon decrease in pressure in the connecting passageway 52 by application of suction thereto, such passageway 52 is opened to the vent passageway 62, as shown in FIG. 9.

With such an arrangement, when the self-inflating bag 60 is manually squeezed, as shown in FIG. 5, gas therefrom flows into the housing 10 into the space between the latter and the bellows 16, thereby ensuring that the nonreturn valve 44 remains closed and causing at least partial collapse of the bellows 16. Accordingly, fresh gas from the gas supply duct 34 passes by way of the filter 40, the fresh gas tube 38 and the respiration tube 36 to the patient to inflate his lungs.

When the patient now breathes out, firstly the bellows 16 expands until arrested by the stop disc 30, and thereafter the non-return valve 44 opens to permit expired changed gas to pass via outlet 22 and the vacuum passage 54 to the vacuum line which may, for example, be part of a vacuum system (not illustrated) which serves to eliminate free anaesthetic gases from the atmospheric area in which the apparatus is being used. This is illustrated in FIG. 6 from which it will be seen that whilst the patient is exhaling, the self-inflating bag 60 is drawing in fresh atmospheric air by way of the vent passageway 62.

Accordingly, it will be understood that by providing the valve arrangement 50 fitted with the self-inflating bag 60, one converts the embodiment of respiration apparatus of FIGS. 1 to 4 in a very simple manner to enable it to be controlled manually, with the patient's lungs being expanded upon squeezing of the self-inflating bag 60, and exhalation occuring upon subsequent releases of the bag 60. In this use of the apparatus, the ventilator, connected to the ventilator passageway 56, is not employed. Accordingly, it will be understood that the presence of such ventilator is optional, and it can be omitted if desired, according to the intended use of the apparatus.

Conversely, if the ventilator is present and made use of, the self-inflating bag 60 is not employed, so that the latter, too, is optional.

Referring now to FIGS. 7 and 8, these illustrate the apparatus being operated with gas under pressure supplied by the ventilator which may conform substantially to those described in the specification of my aforementioned Patent No. 1207661. The breathing connection of the ventilator is connected to the ventilator passageway 56, and the gas inlet connection of the ventilator is continuously supplied with gas under pressure. Accordingly, the operation of such ventilator is such as to provide, at regular intervals, momentary opening of its breathing connection with its gas supply, thereby to provide a momentary increase in pressure in the housing 10 of the apparatus of the invention, as shown in FIG. 7 in the drawings, with consequential compression or partial collapse of the bellows 16 and inflation of the patient's lungs; upon the ventilator subsequently shutting off its breathing connection from the gas supply, the condition of FIG. 8 is obtained and gas exhaled by the patient firstly passes into the bellows 16 and then the excess expelled by way of the housing to the vacuum connection 54. Accordingly, the action of the apparatus when the ventilator is employed is substantially the same as when the self-inflating bag 60 is employed, save that with the latter the lung inflation and exhalation is controlled manually, whilst with the former it is controlled automatically in conformity with the operation of the ventilator and at a rate dependent upon the adjustment of the ventilator.

FIGS. 9 and 10 show the operation of the apparatus with the patient breathing spontaneously, so that no use is made of either the bag 60 or the ventilator. As shown in FIG. 9, upon the patient inhaling, the bellows 16 collapses and air is drawn into the housing 10 by way of the connecting passageway 52 and the air passageway 62. Upon exhalation, as previously described, excess gas from the housing 10 leaves the latter by way of the connecting passageway 52 and the vacuum passageway 54.

The invention is not confined to the precise details of the foregoing examples and variations may be made thereto. Thus, for instance, the expansible container does not have to be in the form of a bellows, but could comprise an inflatable bag or a piston/cylinder arrangement, and the disposition thereof does not have to be such that expansion results in upward movement, it being possible for the arrangement to be such that horizontal or downward movement is obtained. The non-return valve 44 can, if desired, alternatively be a spring-loaded valve, or a mechanically, pneumatically, hydraulically or electrically-operated valve; furthermore it need not be positioned actually within the base plate of the housing as shown but could be remotely disposed, provided it has an appropriable operating mechanism associated therewith. The tubing employed in the apparatus may be of rubber or plastics, either disposable or re-usable, and may incorporate appropriate bacteriological filters as desired.

I claim:

1. Anaesthetist's respiration apparatus comprising a housing enclosing an expansible and contractible container, the housing defining a continuously open and unvalved fresh gas supply passageway to the interior of the container, a respiration tube, adapted for providing a respiration gas supply to a patient, having a continuously open connection to the interior of the container and also being connected by a branch connection therefrom to the housing outside of the container by way of a non-return valve permitting flow only in the direction from the respiration tube into the housing, the volume within the container and the respiration tube between the branch connection and the container comprising a reservoir for an initial volume of gas exhaled by a patient, means for adjusting the extent by which the container may expand, and an unvalved outlet opening from the housing outside of the container for flow from the housing of gas exhaled by a patient, in excess of said initial volume, communicated to the housing externally of the container via the branch connection and the non-return valve.

2. Apparatus as in claim 1 wherein the container is an axially expansible and contractible bellows, and the adjustment means defines a stop which limits extension of the bellows, and wherein the container must hit the adjustable stop before the non-return valve will open.

3. Apparatus as claimed in claim 1 including a valve arrangement coupled to the housing outlet and having (1) a connecting passageway which is connected to the outlet, (2) a vacuum passageway adapted to be connected to suction means, (3) a third passageway for connection either to an automatic ventilator or to a self-inflating bag, the valve arrangement providing for:
   a. increase in pressure in the third passageway causing such passageway to connect with the connecting passageway;
   b. increase in pressure in the connecting passageway causing such passageway to connect with the vacuum passageway;
   c. decrease in pressure in the connecting passageway causing such passageway to be opened to atmosphere.

4. Apparatus as claimed in claim 3 wherein the valve arrangement is so arranged that a decrease in pressure in the third passageway causes such passageway to connect with atmosphere.

5. Apparatus as claimed in claim 3 including an additional passageway defined by the valve arrangement and in which the valve arrangement provides for coupling of the additional passageway to the connecting passageway and to atmosphere in the same manner as provided for as to the third passageway for the same pressure conditions as are pertinent to the third passageway.

6. Apparatus according to claim 3 wherein the housing is arranged relative to the container and the outlet from the housing so that gases supplied to the housing via the outlet for contracting the container and such gases as may pass through the container from the interior thereof to the interior of the housing are extractible from the housing via the outlet.

7. In an anaesthetist's respiration apparatus which includes an expansible and contractible container and gas flow means associated with the container including a continuously open and unvalved fresh gas supply passageway to the interior of the container, a patient respiration tube continuously open to the interior of the container for flow of gas to and from the container from and to a patient, and a patient exhalation tube connected to the patient respiration tube remote from the container and equipped with a check valve regulating flow through the exhalation tube to flow only away from the respiration tube, the improvement comprising a housing enclosing the container and defining a chamber about the container, the exhalation tube being connected only from the respiration tube to the chamber via the check valve, means for adjusting the extent by which the container may expand within the chamber, and an unvalved outlet through the housing from the chamber, in which the volume of the expanded container and of the respiration tube provides a reservoir for an initial volume of gas exhaled by a patient, and in which the remaining volume of gas exhaled by a patient is applied to the chamber.

\* \* \* \* \*